(12) United States Patent
Bisgrove et al.

(10) Patent No.: US 9,945,850 B2
(45) Date of Patent: Apr. 17, 2018

(54) LATERAL FLOW ASSAYS FOR NON-DIAGNOSTIC ANALYTES

(75) Inventors: Dwayne Bisgrove, Mountain View, CA (US); Hiroaki Sagawa, Mountain View, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 563 days.

(21) Appl. No.: 13/208,267

(22) Filed: Aug. 11, 2011

(65) Prior Publication Data

US 2012/0040336 A1  Feb. 16, 2012

Related U.S. Application Data

(60) Provisional application No. 61/415,218, filed on Nov. 18, 2010, provisional application No. 61/373,110, filed on Aug. 12, 2010.

(51) Int. Cl.
*A61K 38/00* (2006.01)
*G01N 33/558* (2006.01)
*C07K 14/005* (2006.01)

(52) U.S. Cl.
CPC ........ *G01N 33/558* (2013.01); *A61K 38/00* (2013.01); *C07K 14/005* (2013.01)

(58) Field of Classification Search
CPC .. C12Q 1/6844; C12Q 2527/125; C12Q 1/24; C12Q 1/6806; C12Q 1/6888; C12Q 1/689; G01N 33/558; G01N 33/54386; G01N 15/147; G01N 15/1484; G01N 33/52; G01N 33/53; G01N 33/5302; G01N 33/56911; G01N 33/05
See application file for complete search history.

(56) References Cited

U.S. PATENT DOCUMENTS

| | | | |
|---|---|---|---|
| 6,924,153 B1 * | 8/2005 | Boehringer | G01N 33/558 422/420 |
| 2003/0087271 A1 * | 5/2003 | Ebersole et al. | 435/6 |
| 2004/0110167 A1 | 6/2004 | Gerdes et al. | |
| 2005/0227275 A1 | 10/2005 | Jung et al. | |
| 2006/0160078 A1 | 7/2006 | Cardy et al. | |
| 2009/0047673 A1 | 2/2009 | Cary | |
| 2009/0305290 A1 | 12/2009 | Sambursky et al. | |
| 2010/0136531 A1 | 6/2010 | Garthwaite et al. | |

FOREIGN PATENT DOCUMENTS

| | | |
|---|---|---|
| EP | 1798556 A1 | 6/2007 |
| EP | 1933144 A1 | 6/2008 |
| JP | 8-505224 A | 6/1996 |
| JP | 2005532827 A | 4/2005 |
| JP | 2005525085 A | 8/2005 |
| JP | 2008500820 A | 1/2008 |
| JP | A2008508863 | 3/2008 |
| JP | 2009502134 A | 1/2009 |
| WO | WO2005111221 | 11/2005 |
| WO | WO2006064847 | 6/2006 |
| WO | WO2008099148 | 8/2008 |
| WO | WO 2010061772 A1 | 6/2010 |

OTHER PUBLICATIONS

Aldus et al., Principles of some novel rapid dipstick methods for detection and characterization of verotoxigenic *Escherichia coli*, 2003, Journal of Applied Microbiology, vol. 95, pp. 380-389.*
Peng et al., Development of an Immunochromatographic Strip for Rapid Detection of H9 Subtype Avian Influenza Viruses, 2008, Clinical and Vaccine Immunology, vol. 15, No. 3, pp. 569-574.*
Wan and Perez, Amino Acid 226 in the Hemagglutinin of H9N2 Influenza Viruses Determines Cell Tropism and Replication in Human Airway Epithelial Cells, 2007, Journal of Virology, vol. 81, No. 10, pp. 5181-5191.*
Richardson et al., Enhanced Protection against Ebola Virus Mediated by an Improved Adenovirus-Based Vaccine, 2009, PLoS one, vol. 4, No. 4, e5308.*
Lin et al., "Distinct Antiviral Roles for Human 2',5'-Oligoadenylate Synthetase Family Members against Dengue Virus Infection", The Journal of Immunology, vol. 183, No. 12, pp. 8035-8043 (2009).
Nabatiyan et al., "A Lateral Flow-Based Ultra-Sensitive p24 HIV Assay Utilizing Fluorescent Microparticles", Journal of Acquired Immune Deficiency Syndromes, vol. 53, No. 1, pp. 55-61 (2010).
"Product Manual Introduction; Quicktiter(TM) Lentivirus Titer Kit", Cell Biolabs, Inc., http://www.cellbiolabs.com/sites/default/files/VPK-107-lentiviral-titer-p24-elisa-kit.pdf, (Oct. 2013).
"Total vector concentration using anti-p24 immunoassay", http://tronolab.epfl.ch/webdav/site/tronolab/shared/LVPU/p24titration.html, (Jun. 2010).
Decision of Refusal issued in Japanese patent application No. 2013-524235, dated Jun. 3, 2014, 4 pages.
Ngom et al. "Development and application of lateral flow test strip technology for detection of infectious agents and chemical contaminants: a review", Analytical and Bioanalytical Chemistry, vol. 397, No. 3, Apr. 27, 2010, pp. 1113-1135.
"RIDA Quick Aflatoxin", Mar. 24, 2006, 14 pages, Retrieved from the Internet: http://www.shp.hu/hpc/userfiles/r-biophaim/r5204_quick_aflatoxin_06_03_24.pdf (retrieved on Nov. 12, 2014).
Blesch A. "Lentiviral and MLV based retroviral vectors for ex vivo and in vivo gene transfer", Methods, Academic Press, US, vol. 33, No. 2, Jun. 1, 2004, pp. 164-172.
Josthuma-Trumpie et al. "Lateral flow (immuno)assay: its strengths, weaknesses, opportunities and threats. A literature survey", Analytical and Bioanalytical Chemistry, Springer, Berlin, Germany, vol. 393, No. 2, Aug. 13, 2008, pp. 569-582.

(Continued)

*Primary Examiner* — Benjamin P Blumel
(74) *Attorney, Agent, or Firm* — Otto C. Guedelhoefer, IV; Bret E. Field; Bozicevic, Field & Francis LLP

(57) ABSTRACT

Methods of determining whether a non-diagnostic analyte is present in a non-diagnostic sample are provided. Aspects of the methods include applying a non-diagnostic sample to a sample receiving region of a lateral flow assay device and reading a detection region to determine whether a non-diagnostic analyte is present in the non-diagnostic sample. Also provided are kits that find use in practicing methods of the invention.

21 Claims, 2 Drawing Sheets

(56) References Cited

OTHER PUBLICATIONS

Clontech Laboratories, Inc. "Lenti-X Expression System", Mar. 1, 2010, Retrieved from the Internet: URL: http://cms.takara.co.kr/file/lsnb/46_12-15.pdf (retrieved on May 12, 2016), 4 pages.
Clontech Laboratories, Inc. "Special Offer from Clontech", Jun. 21, 2010, Retrieved from the Internet: URL: http://www.ibric.org/myboard/down.php?Board=enterprise&filename=6clontech.pdf&id=14694&fidx=1 (retrieved on May 12, 2016), 4 pages.
Author Unknown: "lenti-x gostix—Google Search",May 12, 2016, Retrieved from the Internet: URL: https://www.google.de/search?q=lenti-x+gostix&source=lnt&tbs=cdr/D3A1%2Ccd_min%3A %2Ccd_max%3Al2.08.2010&tbm= (retrieved on May 12, 2016), 1 page.
Clontech Laboratories, Inc. "Lenti-X(TM) p24 Rapid Titer Kit User Manual", May 5, 2009, (retrieved on May 12, 2016), pp. 1-12.

* cited by examiner

LATERAL FLOW ASSAYS FOR NON-DIAGNOSTIC ANALYTES

CROSS-REFERENCE TO RELATED APPLICATIONS

Pursuant to 35 U.S.C. § 119 (e) this application claims priority to the filing date of U.S. Provisional Patent Application Ser. No. 61/373,110 filed Aug. 12, 2010 and U.S. Provisional Patent Application Ser. No. 61/415,218 filed Nov. 18, 2010; the disclosures of which applications are herein incorporated by reference.

INTRODUCTION

Various lateral flow assay test strips are utilized to test for the presence of, absence of or quantity of an analyte in a biological sample for diagnostic purposes. Conventional lateral flow test strips feature a solid support on which a sample receiving area and the target capture zones are supported. The solid support material is one which is capable of supporting the sample receiving area and target capture zones and providing for the capillary flow of sample out from the sample receiving area to the target capture zones when the lateral flow test strip is exposed to an appropriate solvent or buffer, which acts as a carrier liquid for the sample. General classes of materials which may be used as supports include organic or inorganic polymers, and natural and synthetic polymers. More specific examples of suitable solid supports include, without limitation, glass fiber, cellulose, nylon, crosslinked dextran, various chromatographic papers and nitrocellulose.

Traditional lateral flow test strips contain one or more target capture lines. These capture lines are located on the strip parallel with the sample receiving area such that the flow of the sample from a sample receiving area sequentially contacts each of the capture lines. During use, sample aliquots are deposited onto a sample receiving area of the lateral flow test strip which may then be exposed to a solvent or carrier liquid which flows across the strip, and carries the sample material across the target capture zones toward an absorbent pad located at the end of the test strip.

The conventional lateral flow test strips are sized to fit in a specific sized plastic housing. The housing typically has an upper part with an opening for sample application to the sample pad and another opening or window over the capture lines to read the results of the assay.

SUMMARY

Methods of determining whether a non-diagnostic analyte is present in a non-diagnostic sample are provided. Aspects of the methods include applying a non-diagnostic sample to a sample receiving region of a lateral flow assay device and reading a detection region to determine whether a non-diagnostic analyte is present in the non-diagnostic sample. Also provided are kits that find use in practicing methods of the invention.

DETAILED DESCRIPTION

Figure 1:
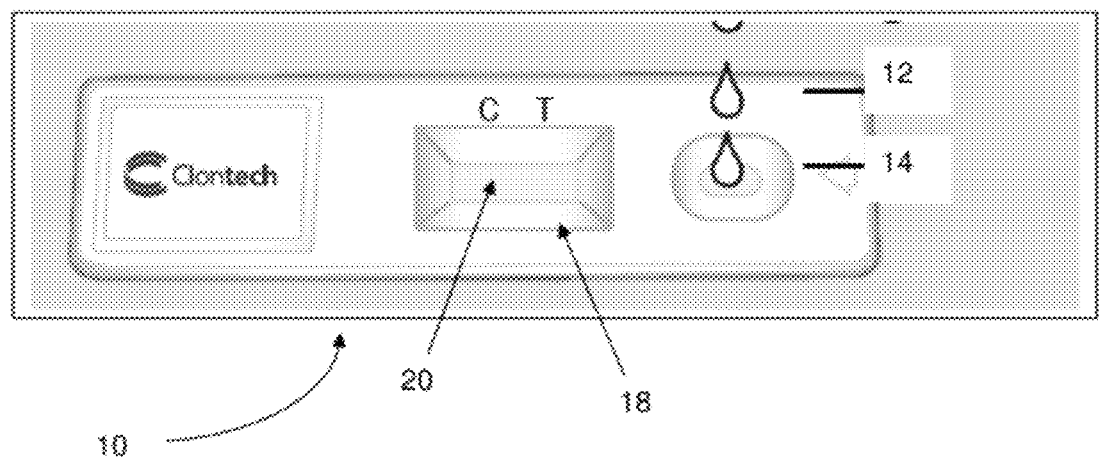
FIG. 1 shows a depiction of a lateral flow assay device according to an embodiment of the invention.

Methods of determining whether a non-diagnostic analyte is present in a non-diagnostic sample are provided. Aspects of the methods include applying a non-diagnostic sample to a sample receiving region of a lateral flow assay device and reading a detection region to determine whether a non-diagnostic analyte is present in the non-diagnostic sample. Also provided are kits that find use in practicing methods of the invention.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

Aspects of the invention include non-diagnostic lateral flow assay methods. Accordingly, methods of the invention are non-diagnostic methods. As the methods are "non-diagnostic methods," they are methods that do not determine a disease (e.g., sickness) or condition (e.g., pregnancy) in a living organism, such as a mammal, e.g., a human. As such, methods of the invention are not methods that are employed to determine whether a living subject has a given disease or condition.

Aspects of the non-diagnostic methods include determining whether a non-diagnostic analyte is present in a non-diagnostic sample. By "non-diagnostic sample" is meant a sample that has not been obtained from or derived from a living multi-cellular organism, e.g., mammal, in order to make a diagnosis. In other words, the sample has not been obtained to determine the presence of one or more disease analytes in order to diagnose a disease or condition. Non-diagnostic samples of interest include those obtained from in vitro sources, e.g., cell cultures, tissue cultures, non-diagnostic animal tissue samples or body fluids (i.e., such samples when not being used for diagnosis), column chromatography devices, etc., e.g., as described in greater detail below. In some instances, non-diagnostic samples that are tested using lateral flow methods of the invention are samples generated in a research laboratory, for example, samples that are obtained from research experiments, including biotechnology research experiments (such as in vitro experiments that may or may not employ living cells, recombinant vectors, synthesized proteins, etc). Examples of research experiment samples include, but are not limited to: cell and tissue cultures (and derivatives thereof, such as supernatants, etc.); non-diagnostic animal tissue samples and body fluids; non-cellular samples, e.g., column eluants, acellular biomolecule (e.g., protein and nucleic acid) synthesis reaction mixtures, nucleic acid amplification reaction mixtures; in vitro biochemical or enzymatic reactions or assay solutions, or products of other in vitro and in vivo reactions; etc. As used herein, research experiment samples exclude environmental samples, e.g., samples that are obtained from the environment in order to determine some quality or aspect of the environment, such as presence of one or more toxins, peptides, proteins, nucleic acids, or small molecules, etc.

One type of non-diagnostic sample that may be assayed in accordance with methods of the invention is a viral vector packaging supernatant. Viral vector packaging supernatants may be generated in a research laboratory in order to transduce target cells. Viral vector packaging supernatants can be generated in a research laboratory by transfecting a packaging cell line, e.g. HEK 293 cells, Sf21 cells, NIH 3T3 cells, and the like, with a competent vector such as, but not limited to: pLVX and its derivatives, pBacPAK8 and its derivatives, pShuttle2 and its derivatives, pRetro-Lib, plasmids derived from MMLV (such as pLXRN, pLNHX, pLNCX, pLNCX2, etc.), and the like. Following transfection, the cells are grown in a suitable growth medium to achieve a desired viral titre. Next, the cell culture may be subjected to centrifuging and/or filtering to separate the supernatant from the cells. The resultant supernatant may include mature virus particles as well as components that are derived from the growth medium, including components found in growth medium such as, but not limited to, Dulbecco's Modified Eagle's Medium (DMEM), glucose, L-glutamine, sodium bicarbonate, fetal bovine serum, sodium pyruvate, and the like. Supernatants of interest may be distinguished from other types of samples, such as physiological samples obtained for diagnostic purposes, based on one or more components that are present in one type of sample but not the other. For example, the supernatants may lack components found in blood derived samples, where blood derived sample components not found in supernatants may include whole cells, clotting factors, antibodies, extracellular proteins, electrolytes, and other entities absent from the non-diagnostic supernatant, e.g., described above.

Another non-diagnostic sample of interest is an in vitro mRNA transcription reaction mixture. As is known in the art, such reaction mixtures may be added to an in vitro translation system to direct synthesis of a protein encoded by the mRNA. In vitro mRNA transcription reaction mixtures can be generated by combining a DNA template with RNA polymerase, nucleotide triphosphates, and an appropriate buffer and incubating the resultant at an appropriate temperature for various durations. A successful, completed reaction mixture may include synthesized mRNA, RNA polymerase, and various other components, such as but not limited to buffers (e.g. tris, tricine, MOPS, HEPES, PIPES, MES, and the like), salts (e.g. sodium chloride, sodium acetate, sodium citrate, sodium phosphate, magnesium chloride, magnesium acetate, potassium chloride, potassium phosphate, potassium acetate, calcium chloride, calcium acetate, calcium phosphate, ammonium chloride, ammonium acetate, and the like), and other small molecules (e.g. nucleotides, reducing agents such as dithiothreitol, and the like).

Non-diagnostic samples of interest also include cell lysates and derivatives thereof, nucleic acid and protein containing lysates from bacteria, yeast, insect or mammalian cells. For example, of interest as non-diagnostic samples are nucleic acid (e.g., DNA and RNA) preparations obtained from lysed bacterial cells. Such compositions can be generated from bacterial cultures by harvesting bacteria, e.g. by centrifugation; resuspending and lysing the bacteria, e.g. by vortexing; precipitating nucleic acid, e.g., DNA, from the lysate, e.g. by adding ethanol; and collecting the precipitated nucleic acid from the lysate, e.g. by column purification or centrifugation and resuspension. A nucleic acid preparation obtained by such means may include DNA and an elution or resuspension buffer (e.g. tris, tricine, MOPS, HEPES, PIPES, MES, and the like) and salts (e.g. sodium chloride, sodium acetate, sodium citrate, sodium phosphate, magnesium chloride, magnesium acetate, potassium chloride, potassium phosphate, potassium acetate, calcium chloride, calcium acetate, calcium phosphate, ammonium chloride, ammonium acetate, and the like). In addition, the composition may further include contaminants, e.g. bacterial endotoxin and the like.

Yet another example of a non-diagnostic sample of interest is a chromatography eluant, such as an eluant from a fast protein liquid chromatography (FPLC) column. Such an eluant can be obtained by applying a sample (e.g., produced from lysates from bacteria, yeast, insect or mammalian cells) using any suitable method known in the art) to a chromatography column, such as a size-exclusion column, affinity column, ion exchange column, hydrophobic interaction column, and the like; moving the protein sample through the column, e.g. using an FPLC pump; and collecting the column eluant in multiple fractions. Any given fraction may include numerous proteins of interest, proteins not of interest, column buffer, and sample buffer (e.g. tris, tricine, MOPS, HEPES, PIPES, MES, and the like), salts (e.g. sodium chloride, sodium acetate, sodium citrate, sodium phosphate, magnesium chloride, magnesium acetate, potassium chloride, potassium phosphate, potassium acetate, calcium chloride, calcium acetate, calcium phosphate, ammonium chloride, ammonium acetate, and the like), and other small molecules (e.g. amino acids, nucleotides, sugars, reducing agents such as dithiothreitol and β-mercaptoethanol, and the like).

Each of these non-diagnostic samples differs from a diagnostic sample by including components not found in diagnostic samples and/or lacking components found in diagnostic samples. In some instances, the contents of a non-diagnostic sample are readily determined because the non-diagnostic sample has been prepared from known starting materials in a research laboratory under defined and controlled conditions and protocols. In contrast, a physiological sample obtained for diagnostic purposes is inherently of unknown content, since individuals vary in terms genetic makeup and exposure to environment conditions.

As mentioned above, methods of the invention are methods of determining whether a non-diagnostic analyte is present in a non-diagnostic sample. As the methods are methods of determining whether a non-diagnostic analyte is present in a non-diagnostic sample, the methods are methods of evaluating a sample in which the analyte of interest may or may not be present. Furthermore, prior to performing the assay, it is unknown whether the analyte is present in the sample. As such, the methods are distinguished from methods in which it is known that the analyte is present, but a specific isotype of the analyte is not known, such as where a sample is assayed to determine the specific isotype of an analyte antibody known to be present in the sample.

By "non-diagnostic analyte" is meant an analyte which is not employed in the methods of the invention to make a diagnosis of a disease or other condition of a living subject, e.g., a mammal. Non-diagnostic analytes of interest may vary widely depending on the particular research experiment with which the methods of the invention are employed. Non-diagnostic analytes of interest include, but are not limited to: vectors, e.g., plasmids, viral vectors, viral particles and the like; expression markers, e.g., reporter enzymes and proteins, such as luciferases, fluorescent proteins, epitope tags and the like; expression products, e.g., proteins, mRNAs, nucleoprotein complexes and the like; therapeutic nucleic acids, e.g., siRNAs, miRNAs, and the like; research contaminants, e.g., mycoplasma, endotoxin, yeast, bacteria, antibiotics (e.g., tetracycline, doxycycline), undesirable growth and differentiation factors and the like; cellular metabolites for assessing cell culture status, etc.

As summarized above, methods of the invention are lateral flow assay methods. As such, methods of the invention include a step of applying a volume of a non-diagnostic sample to a lateral flow assay device, e.g., a lateral flow assay test strip. As the assay devices are "lateral flow" assay devices, they are configured to receive a sample of interest at a sample receiving region and to provide for the sample to move laterally through a bibulous material (i.e., bibulous member) by capillary action to a detection region, such that the sample is wicked laterally through the bibulous member from the sample receiving region to the detection region.

Bibulous members of devices of the invention may be fabricated from any convenient material. Examples of bibulous materials of interest include, but are not limited to: organic or inorganic polymers, and natural and synthetic polymers. More specific examples of suitable solid supports include, without limitation, glass fiber, cellulose, nylon, crosslinked dextran, various chromatographic papers and nitrocellulose.

While the bibulous member and overall configuration of the lateral assay device may vary, in certain embodiments the bibulous member has a strip configuration. Where the bibulous material is configured as a strip, the bibulous member has a length that is longer than its width. While any practical configuration may be employed, in some instances the length is longer than the width by 1.5 fold or more, such as 2-fold or more, e.g., 10 fold or more, including 20-fold or more. In some instances, the length of the bibulous member ranges from 0.5 to 20 cm, such as 1.0 to 15 cm, e.g., 2.0 to 10 cm, while the width ranges 0.1 to 5.0 cm, such as 0.5 to 2.5 cm, e.g., 1 to 2 cm. The thickness of the bibulous member may also vary, ranging in some instances from 0.01 to 0.05 cm, such as 0.1 to 0.4 cm, e.g., 0.1 to 0.25 cm.

In addition to the bibulous member, devices of the invention include a sample receiving region. The sample receiving region may simply be a first region of the bibulous member, e.g., positioned closer to one end of the bibulous member. Alternatively, the sample receiving region may be distinct from the bibulous member, but configured to provide for fluid communication of sample into the bibulous member upon application of sample to the sample receiving region. The sample receiving region may be configured to receive samples of varying volumes, where in some instances the sample receiving region is configured to receive a sample having a volume ranging from 0.1 to 1000 μl, such as 5 to 20 μl and including 50 to 200 μl. In some instances, the sample receiving region may include a metering device configured to meter a specific amount of sample into the bibulous member. Examples of metering devices of interest include those described in United States Published Patent Application Nos.: 20080145272; 20070134810; 20060008847; and 20050227370.

In addition to the sample receiving region, lateral flow assay devices of the invention further include a detection region. A detection region is a region of the bibulous member from which a result may be read during use of the device. The detection region is positioned at some distance downstream from the sample receiving region of the device. By "downstream" is meant the lateral direction that the sample flows by capillary action, i.e., the direction of fluid flow from the sample receiving region. The distance between the sample receiving region and the detection region may vary, ranging in some instances from 0.3 to 15 cm, such as 1 to 15 cm and including 5 to 10 cm, e.g., 1 to 5 cm.

The detection region is a region that includes at least one distinct capture probe region. The capture probe region is a region that includes an amount of capture probe stably associated with the bibulous member in the capture probe region. The size of the capture probe region may vary, and in some instances the capture probe region has an area ranging from 0.01 to 0.5 cm$^2$, such as 0.05 to 0.1 cm$^2$ and including 0.1 to 0.2 cm$^2$. The capture probe region may have a variety of different configurations, where the configuration may be a line, circle, square, or more complex shape, such as a "+", as desired.

As indicated above, the capture probe region includes a capture probe stably associated with the bibulous material of the bibulous member. By "stably associated with" is meant that the capture probe and the bibulous member maintain their position relative to each other in space under the conditions of use, e.g., under the assay conditions. As such, the capture probe and the bibulous member can be non-covalently or covalently stably associated with each other. Examples of non-covalent association include non-specific adsorption, binding based on electrostatic (e.g., ion-ion pair interactions), hydrophobic interactions, hydrogen bonding interactions, and the like. Examples of covalent binding include covalent bonds formed between the capture probe and a functional group present on the bibulous material.

Capture probes are molecules that specifically bind to an analyte of interest. The terms "specific binding," "specifically bind," and the like, refer to the ability of the capture probe to preferentially bind directly to the analyte of interest relative to other molecules or moieties in a solution or reaction mixture that may be present in the bibulous member. In certain embodiments, the affinity between a capture probe and the analyte to which it specifically binds when they are specifically bound to each other in a binding complex is characterized by a $K_D$ (dissociation constant) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M.

A variety of different types of specific binding agents may be employed as the capture probe. Specific binding agents of interest include antibody binding agents, proteins, peptides, haptens, nucleic acids, etc. The term "antibody binding agent" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'$_2$ fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

A given detection region may include a single capture probe region or two or more different capture probe regions, where each of the two or more different capture probe regions includes a capture probe, where the capture probe in each region may be the same (such as is found in the quantitative assay devices as described in greater detail below) or different (such as may be present in multiplex assay devices as described in greater detail below). Where the detection region includes two or more capture probe regions, the regions may be distinct from each other or overlapping, as desired.

In some instances, the bibulous member may include a reporter binding member positioned upstream from the detection region, e.g., either in the sample receiving region or a location between the sample receiving region and the detection region. The distance between the reporter binding member and the detection region may vary, ranging in some instances from 0.3 to 15 cm, such as 1 to 5 cm and including 5 to 10 cm. The reporter binding member, when present, is non-stably associated with the bibulous member. By "non-stably associated" is meant that while the reporter binding member may be stationary relative to the bibulous member prior to sample application, upon sample application and sample wicking through the bibulous binding member, the reporter binding member is free to react with analyte present in the sample and to move with the sample through the bibulous member by capillary action. As such, the reporter binding member moves laterally through the bibulous member under the bulk fluid flow forces.

Reporter binding members of interest include a specific binding member and a signal producing system member. In the reporter binding member, the specific binding member and the signal producing system member are stably associated with each other, e.g., via covalent bonding.

The specific binding member may vary depending on whether the assay has a competitive or sandwich format. For competitive formats, the binding member is a moiety that competes with the analyte of interest for binding to the capture probe in the detection region. The binding member may be the analyte or a fragment thereof. For sandwich formats, the binding member specifically binds to the analyte at a location that is different from the location to which the capture probe binds. As such, the binding member and the capture probe may simultaneously bind to the analyte of interest. In these sandwich formats, the analyte specific binding moiety may be any moiety that specifically binds to the analyte of interest. Specific binding members of interest include antibody binding members, proteins, peptides, haptens, nucleic acids, etc. The term "antibody binding member" as used herein includes polyclonal or monoclonal antibodies or fragments that are sufficient to bind to an analyte of interest. The antibody fragments can be, for example, monomeric Fab fragments, monomeric Fab' fragments, or dimeric F(ab)'$_2$ fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies.

In addition to the binding member, the reporter binding member further includes a member of a signal producing system. The member of the signal producing system may vary widely depending on the particular nature of the lateral flow assay and may be any directly or indirectly detectable label. Suitable detectable labels for use in the above methods include any moiety that is detectable by spectroscopic, photochemical, biochemical, immunochemical, electrical, optical, chemical, or other means. For example, suitable labels include biotin for staining with labeled streptavidin conjugate, fluorescent dyes (e.g., fluorescein, Texas red, rhodamine, green fluorescent protein, and the like), radiolabels (e.g. $^3$H, $^{125}$I, $^{35}$S, $^{14}$C, or $^{32}$P), enzymes (e.g., horseradish peroxidase, alkaline phosphatase and others commonly used in an ELISA), and colorimetric labels such as colloidal gold or colored glass or plastic (e.g., polystyrene, polypropylene, latex beads). Patents that describe the use of such labels include U.S. Pat. Nos. 3,817,837; 3,850,752; 3,939,350; 3,996,345; 4,277,437; 4,275,149; and 4,366,241. See also Handbook of Fluorescent Probes and Research Chemicals (6th Ed., Molecular Probes, Inc., Eugene Oreg.). Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

In some instances, the lateral flow assay device may further include a control region. The control region is located downstream from the sample receiving region, and may be located upstream or downstream from the detection region, as desired. The control region contains immobilized control agents. The immobilized control agents bind specifically to mobile control binding agents to form a control binding pair, e.g., as described in U.S. Pat. No. 6,136,610. Control binding pairs of interest act as internal controls, that is, the control against which the analyte measurement results may be compared on the individual test strip. Although, in general, any conventional controls can be used herein, in some instances control compounds that do not exist in the sample or do not immunologically cross-react with compounds that exist in the sample are employed. Examples of suitable control binding pairs of interest include, but are not limited to: Mouse IgG/anti-mouse IgG, chicken IgY/anti-chicken IgY, etc. Either member of these pairs may be the immobilized control agent, with the other being the control binding agent. A given lateral flow assay device may have a single control region or two or more different control regions, where the immobilized control agents of each region may be the same or different. The control binding agent may optionally be non-stably associated with the bibulous member at a location that is upstream from the control region, e.g., at a location that is the same as or different from the reporter binding agent.

Optionally, the lateral flow assay device may include an absorbent pad downstream from the detection region and any control region, e.g., at the end distal from the sample receiving region, where the absorbent pad is configured to absorb fluid and reagents present therein that have flowed through the bibulous member.

Where desired, the component parts of the lateral flow assay device may be present in a suitable housing. The housing may be configured to enclose the bibulous member and other assay components. The housing may be fabricated from any suitable material, where the material may be a material that is sufficiently rigid to maintain the integrity of the bibulous member and other components housed therein and also inert to the various fluids and reagents that contact the housing during use. Housing materials of interest include plastics. The housing may include a port or analogous structure configured to allow sample application to the sample application region and a window configured to allow viewing of the detection region. The housing may further include markings, e.g., detection region and control region markings (e.g., "T" and "C"), etc.

A lateral flow assay device according to an embodiment of the invention is depicted in FIG. 1. In FIG. 1, lateral flow assay device 10 includes a housing 12 that encloses a bibulous member. Sample is applied to sample receiving region 14 via sample port 16. Also shown is viewing window 18 which allows for visualization of the detection region 20.

In practicing methods of the invention, the non-diagnostic sample of interest is applied to the sample receiving region of the lateral flow assay device. In some instances, the non-diagnostic sample is combined with an amount of reporter binding agent and/or control binding agent, e.g., where either or both of these components are not already present in the device. When the sample is combined with either or both of these assay components, the combination may be achieved using any convenient protocol. The amount of these agents, when combined with the sample, may vary, with the desired amount being readily determined, e.g., via standard methods known in the art, The amount of sample that is applied to the sample receiving region may vary, so long as it is sufficient to provide for the desired lateral flow and operability of the assay. The sample may be applied to the sample receiving region using any convenient protocol, e.g., via dropper, pipette, syringe and the like. As such, a first step in methods of the invention is applying the non-diagnostic sample to a sample receiving region of a test lateral flow assay device. In addition to applying sample, the methods may further include applying a quantity of a suitable liquid, e.g., buffer, to provide for adequate fluid flow through the bibulous member. Any suitable liquid may be employed, including but not limited to buffers, cell culture media (e.g., DNEM), etc. Buffers of interest include, but not limited to: tris, tricine, MOPS, HEPES, PIPES, MES, PBS, TBS, and the like. Where desired, detergents may be present in the liquid, e.g., NP-40 or TWEEN™ detergents.

Following sample application, the sample is allowed to laterally flow through the bibulous member and detection region, and the detection region is then read to determine whether the non-diagnostic analyte is present in the non-diagnostic sample. The detection region may be read after a predetermined period of time following sample application, where this period of time may range from 10 sec to 1 hour, such as 30 sec to 30 min, e.g., 30 sec to 1 min. The detection region is read using a protocol that depends on the nature of the detectable product of the signal producing system. Radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. Accordingly, in those instances where the detectable product of the signal producing system is a colored label, the method may include visually inspecting the detection region, e.g., through the viewing window of a housing of the device. As such, a subsequent step in methods of the invention includes reading a detection region of the test lateral flow assay device to determine whether the non-diagnostic analyte is present in the non-diagnostic sample.

Figure 2A:
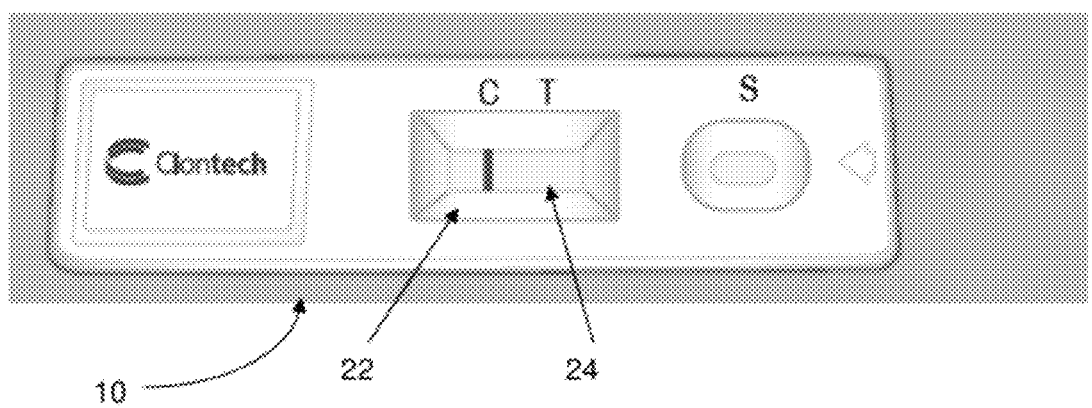
FIGS. 2A and 2B illustrate negative and positive results, respectively, obtained with the device illustrated in FIG. 1.
Figure 2B:
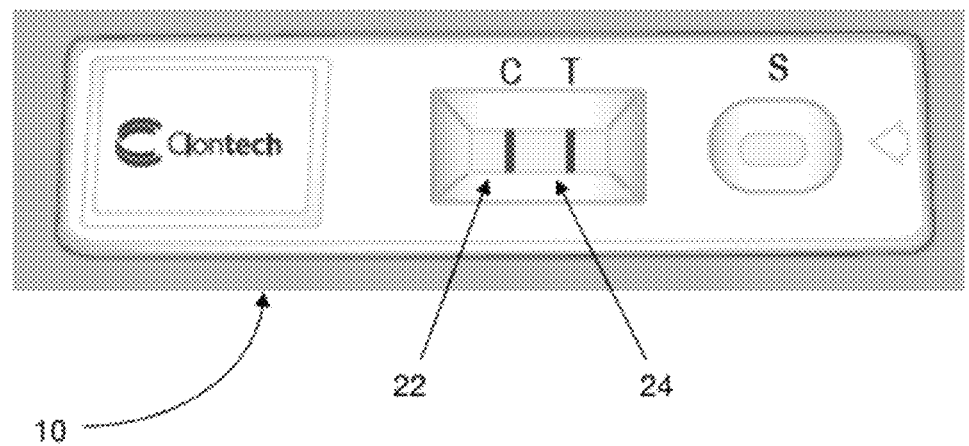

FIGS. 2A and 2B provide illustrations of the device shown in FIG. 1 in which a negative result has been obtained (FIG. 2A) and positive result has been obtained (FIG. 2B). In FIG. 2A, the only stripe visible and therefore detected in the detection region 20 of the device 10 is the internal control stripe 22. The presence of the control stripe 22 and absence of any test stripe in region "T" 24 indicates that no analyte was present in the assayed sample, but the assay was working correctly as demonstrated by the presence of the internal control stripe 22. In FIG. 2B, both the internal control stripe 22 and the test strip 24 are visible and therefore detected in the detection 20 region of device 10. The presence of the control stripe 22 and the test stripe 24 in region "T" indicates that analyte was present in the assayed sample and the assay was working correctly as demonstrated by the presence of the internal control stripe 22.

Where desired, methods may further include applying a control sample to a sample receiving region of a control lateral flow assay device and reading a detection region of the control lateral flow assay device to obtain a result. In these embodiments, the control lateral flow assay device is identical (e.g., a second lateral flow device from the same production lot as the test lateral flow device) to the test lateral flow assay device. The control sample is a fluid sample comprising a known amount of the non-diagnostic analyte of interest. As such, these embodiments employ running a complete control assay using a lateral flow assay device that is the same as the test lateral flow assay device.

Methods of the invention may provide qualitative or quantitative results. Qualitative results include results that provide a simple "yes" or "no" determination of whether the analyte is present in the sample being assayed. Qualitative results also include results that are positive if the amount of analyte in the sample exceeds a pre-determined threshold.

In some embodiments where lateral flow assay device is configured to provide qualitative results, such as those where the analyte needs to be at a certain minimum concentration to be used in subsequent procedures, the assay device may be configured to have lower sensitivity than a comparable lateral flow assay device that is configured to detect the presence of the analyte at any concentration. As such, in certain instances where qualitative results in the format of an analyte simply being present in an amount that exceeds a pre-determined threshold are desired, the assay device may be configured to have a sensitivity that is not sufficient to provide detection below the threshold. If the assay device is too sensitive, then there is a risk of a false positive result where an analyte that is too low in concentration to be useful nonetheless yields a positive result. This sensitivity can be set to any minimum amount of analyte in the non-diagnostic sample. In addition, in certain embodiments, multiple assay devices (e.g., in the form of test strips) may be supplied (e.g., in the form of a kit as reviewed in greater detail below) each with the same antibody and analyte but with different sensitivities depending on the necessary threshold for analyte utility. These types of qualitative embodiments are distinguished from diagnostic assay devices which are configured to be sensitive for all levels of analyte in a given sample. The desired sensitivity may be provided in a given device using any convenient protocol, e.g., by providing an appropriate amount of capture agent in the detection region, etc.

In contrast, quantitative results provide some measurement of how much of the analyte is present in the sample being assayed. Accordingly, a quantitative result provides at least an approximation of the amount of the analyte of the interest that is present in the sample being assayed. To provide for quantitative results, the detection region may include two or more distinct capture probe regions that include the same or different amounts of the same capture probe. As such, if the amount of analyte in the sample exceeds the amount of the analyte that can be captured in the first capture region, the remaining free analyte will move to the second capture region. The resultant positive results from the both regions provide a quantitative measurement of the amount of analyte in the sample. By having a series of regions, which may be a gradient of two or more capture regions each having differing (such as decreasing) amounts of capture probe, a quantitative measurement of the analyte in the sample may be obtained. Alternatively, quantitative measurements can be obtained by densitometry. In this case, only one capture region is necessary.

In some instances, the method is a multiplex assay in which the presence of two or more distinct (i.e., different) non-diagnostic analytes (e.g., that differ from each other by molecular formula) in the sample is determined, either qualitatively or quantitatively. The number of distinct analytes that may be detected in a given multiplex assay may vary, ranging in some instances from 1 to 12, such as 1 to 2 and including 2 to 4. To provide for multiplex analysis, the configuration of the lateral flow assay device may vary. For example, the lateral flow assay device may include a single sample receiving region and a detection region that includes capture probes for each of the two or more non-diagnostic analytes, where the different capture probes may be present in the same capture region or in different capture regions, e.g., depending on whether the labels employed for each analyte are distinguishable from each other. Accordingly, in these instances the lateral flow assay device may include a single flow lane linking the sample receiving region to the detection region. Another multiplex configuration of interest includes a separate sample receiving region and detection region for each of the two or more non-diagnostic analytes of interest. Accordingly, a given lateral flow assay device of interest may include two or more distinct flow lanes, each having its own sample receiving region and detection region. Other configurations are also possible, including a configuration having multiple flow lanes extending from a single sample receiving region to multiple detection regions, where a separate detection region is provided for each analyte of interest. Additional details regarding multiplex configurations are provided in U.S. Pat. No. 6,037,127, the disclosure of which is herein incorporated by reference.

As mentioned above, in some instances the analyte detection assays are employed as one step in a multi-step research protocol, where the protocol at least includes a further step either before or after the step of analyte detection of the present invention. Therefore, aspects of the invention include a research protocol that includes a first step, an analyte detection step and then a subsequent step. For example, in some instances methods of the invention include a step of preparing the non-diagnostic sample, a step of testing the non-diagnostic sample for the non-diagnostic analyte of interest and then a step of further using the non-diagnostic sample in a research procedure, e.g., a further method performed in a laboratory.

For example, in one embodiment, the analyte to be detected may be a viral vector (e.g., viral particle) that is present in a viral vector packaging supernatant. In this case, the analyte detection step may be preceded by generation of a viral vector supernatant that is generated for use in viral expression protocols, such as those used in lentiviral expression systems, baculoviral expression systems, adenoviral expression systems, retroviral expression systems, and the like. In performing these types of protocols, a researcher may first clone a gene of interest into a vector, such as pLVX and its derivatives, pBacPAK8 and its derivatives, pShuttle2 and its derivatives, pRetro-Lib, plasmids derived from MMLV (such as pLXRN, pLNHX, pLNCX, pLNCX2, etc.), and the like. Following this cloning step, the researcher may then co-transfect the product into host cells, such as HEK 293 cells, Sf21 cells, NIH 3T3 cells, and the like along with any protocol-specific packaging reagents, e.g. Lenti-X™ packaging mix, BacPAK6 viral DNA, envelope vectors (e.g. pVSV-G, pEco, pAmpho, p10A1, etc.) and the like. Following transfection, the packaging cells may be allowed to grow for a number of hours, e.g. 24-72 hours. During this period, mature virus particles containing a gene of interest form in the infected cells and, in some cases can be found in the growth medium, or else packed within the cell itself. Following growth, the researcher centrifuges or filters the growth medium to obtain the supernatant fraction, or, in the case of virus produced inside the cells, the researcher may lyse the cells using any appropriate procedure known in the art.

At this stage, an analyte detection step may be used to ensure that virus is present in the harvested supernatant prior to subsequent transduction steps. For example, Lenti-X™ GoStix™ lateral flow assay strips, e.g., as described in greater detail in the experimental section, below, can be used to detect lentiviral p24 in harvested supernatant by applying a small volume of the supernatant, e.g. 20 µL, to a strip's sample receiving region, then allowing the supernatant to pass through the bibulous member to the detection region. If the supernatant contains a quantity of mature lentivirus at a concentration sufficient to support transduction of target cells, e.g. >$5 \times 10^5$ infectious units per milliliter (IFU/mL), then the capture probe region will capture lentiviral p24 attached to reporter binding member in sufficient quantities to produce a visible signal and indicate the presence of the lentivirus. The researcher can then use the supernatant to reliably transduce target cells. Other lateral flow assays can be employed to test for the presence of various other viruses in supernatant, such as baculovirus, retroviruses, and the like, in an analogous manner. A quantitative estimate of the amount of virus present in the sample can be obtained using strips comprising multiple capture probe regions, or by densitometry, as described above.

In some instances, the analyte to be detected may be an epitope tag, e.g. 6xHN, 6-His, FLAG, c-Myc, HA, and the like, attached to an expressed protein. Prior to the detection step, a researcher may express epitope-tagged proteins in one of a variety of systems, such as E. coli, S. cerevisiae, viral expression systems, and the like. The researcher may then opt to purify the protein using methods such as chromatography (e.g. affinity, ion exchange, size-exclusion, and the like), selective precipitation, filtration, and the like. A detection step may then be performed by applying a fraction of the sample to the sample receiving region of a lateral flow assay comprising a capture probe, e.g. tag-specific monoclonal or polyclonal antibody and the like, and reporter binding agent, e.g. monoclonal or polyclonal antibody conjugated to gold or latex colloids and the like, that each specifically bind to the epitope tag. If sufficient quantities of the epitope-tagged protein are applied to such a lateral flow assay, then a visible signal will indicate the presence of the epitope tag. A quantitative estimate of the amount of expressed protein present in the sample can be obtained using strips comprising multiple capture probe regions, or by densitometry, as described above.

In yet another embodiment, the analyte to be detected may be a laboratory contaminant, e.g. mycoplasma and the like. In this case, the analyte detection step may be employed at any time during a multi-step research protocol to test for the presence of a contaminating agent. The detection step's indication of the absence or presence of such contaminating agents will dictate whether any subsequent experiment sensitive to such agents, e.g. tissue culture, may proceed or must be aborted. A quantitative estimate of the amount of expressed protein present in the sample can be obtained using strips comprising multiple capture probe regions, or by densitometry, as described above.

In yet another embodiment, the analyte to be detected may be a reporter protein, e.g. luciferase, fluorescent proteins (such as green fluorescent protein and the like), β-galactosidase, β-glucuronidase, and the like. For example, a researcher may create an expression construct containing a reporter gene such as those listed above driven by an experimental transcription factor, then culture cells under various stress conditions (such as starvation, heat or cold treatment, nutrient or salt abundance or deprivation, and the like) and subsequently harvest the cellular supernatant. The analyte detection step can be used to determine the presence, absence, or quantity of the expressed reporter protein, thus allowing the researcher to determine whether the transcription factor was active under the stress conditions, whether to continue with subsequent steps of the protocol, etc. Alternatively, the method may be employed to confirm transfection. For example, a secreted protein like metridia luciferase may be assayed to confirm successful transfection—e.g. by detecting presence of the metridia luciferase in the supernatant of successfully transfected cells. Confirmation of transfection may then be used as indication that the cells are suitable for use in further experiments. Where desired, a quantitative estimate of the amount of expressed protein present in the sample can be obtained using strips comprising multiple capture probe regions, or by densitometry, as described above.

In yet another embodiment, the analyte to be detected may be a sample contaminant, such as bacterial endotoxin, culture contaminants such as mycoplasma, and the like. In this case, a researcher may prepare a sample of DNA, protein, or another molecule from a bacterial (or other appropriate, e.g., cell culture) source and wish to check for contamination prior to using the preparation in subsequent experiments. The researcher may use an analyte detection step to ensure that the preparation is free of contaminant, e.g., endotoxin, mycoplasma, etc., prior to further experiments involving the composition of interest.

Kits

Additional aspects of the invention include kits, e.g., for use in practicing methods of the invention, such as determining the presence of one or more non-diagnostic analytes in a non-diagnostic sample. Kits may include at least two identical lateral flow assay devices and a control for a non-diagnostic analyte of interest, where each of these components is described in greater detail above. The kits may further include one or more additional assay components, such as reagents (e.g., reporter binding member, control binding agent, etc.), buffers, sample applicators, etc. The various reagent components of the kits may be present in separate containers, or some or all of them may be precombined into a reagent mixture.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), etc., on which the information has been recorded. Yet another form of these instructions that may be present is a website address which may be used via the internet to access the information at a removed site.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); nt, nucleotide(s) and the like.

A. Generation of Lentiviral Vector Packaging Supernatant

A gene of interest is cloned into plasmid vector pLVX-Puro using standard molecular biology techniques known to one of skill in the art. The resulting construct is then amplified by transformation into *E. coli* and recovered and purified using standard protocols. In a first tube, 7 μl of this vector DNA at a concentration of 1 μg/μl is combined with 557 μl of Xfect Reaction Buffer and 36 μl of Lenti-X™ HTX Packaging Mix (both available from Clontech as part of Lenti-X™ HTX Packaging System, Cat. No. 631247). In a second tube, 592.5 μl of Xfect Reaction Buffer is combined with 7.5 μl of thoroughly vortexed Xfect Polymer (both available from Clontech as part of Lenti-X™ HTX Packaging System, Cat. No. 631247). Each tube is vortexed separately, then the contents of the tubes are combined and vortexed for 10 sec. The resulting mixture is incubated for 10 min. at room temperature. The entire 1200 μl of mixture is then added drop-wise to Lenti-X™ 293T cells (Clontech Cat. No. 632180) that have previously been seeded at 4-5×10$^6$ cells/100 mm plate in 10 ml of growth medium (90% Dulbecco's Modified Eagle's Medium with 4.5 g/l glucose, 4 mM L-glutamine, 3.7 g/l sodium bicarbonate; and 10% tetracycline-free fetal bovine serum; brought to 1 mM sodium pyruvate prior to use) and grown overnight at 37° C. and 5% $CO_2$. The resulting cell mixture is incubated at 37° C. at least 4 hours to overnight, then the medium is exchanged for 10 ml of fresh growth medium. The cells are allowed to grow in this fresh medium at 37° C. for 24-48 hours. After this incubation period, the supernatant is harvested by centrifuging the growth medium at 500×g for 10 min. and removing the supernatant from the cell pellet.

B. Detection of Lentivirus in the Supernatant by Lateral Flow Assay

20 μl of the supernatant is then applied to the sample receiving region of a Lenti-X™ GoStix™ lateral flow assay stick (Clontech Cat. No. 631243). Four drops of a chase buffer is then added to the sample receiving area. After 2-10 minutes at room temperature, the test and control regions are visualized. If sufficient liquid has been applied to the sample receiving area, a reddish colored band will appear at the control line. If p24 protein is present in the sample, a reddish band is observed at the test line. The reddish colored test band is due to retention of immunocomplexes of p24 protein and gold particles coated with anti-p24 antibody (detection antibody). As a positive control, a second assay can be run in parallel. In this case, four drops of chase buffer are added to the p24 control tube which contains lyophilized recombinant p24 protein. The chase buffer with solubilized p24 protein is the transferred to the sample receiving area. After 2-10 minutes at room temperature, the test and control regions are visualized. Reddish colored bands at both the control and test detection regions confirm that the assay is working correctly.

What is claimed is:

1. A method of determining whether a recombinant virus is generated from a packaging cell line, the method comprising:
    (a) transfecting a viral vector plasmid comprising a heterologous coding sequence into a packaging cell line for the viral vector plasmid to produce a recombinant viral vector packaging supernatant from the packaging cell line;
    (b) applying a sample of the viral vector packaging supernatant to a sample receiving region of a test lateral flow assay device; and
    (c) reading a detection region of the test lateral flow assay device to determine whether the recombinant virus is present in the sample, wherein the detection region comprises a capture binding member that specifically binds to the recombinant virus, wherein the recombinant virus is selected from the group consisting of a retrovirus, a baculovirus and an adenovirus.

2. The method according to claim 1, wherein the method further comprises applying a control sample to a sample receiving region of a control lateral flow assay device and reading a detection region of the control lateral flow assay device, wherein the control lateral flow assay device is identical to the test lateral flow assay device.

3. The method according to claim 1, wherein the method qualitatively determines whether the recombinant virus is present in the sample.

4. The method according to claim 1, wherein the method quantitatively determines whether the recombinant virus is present in the sample.

5. The method according to any of the preceding claims, wherein the detection region comprises two or more distinct capture probe regions.

6. The method according to claim 1, wherein the method is a method of determining whether two or more different analytes of the recombinant virus are present in the sample.

7. The method according to claim 6, wherein the test lateral flow assay device comprises a single sample receiving region and a detection region comprising capture probes for each of the two or more different analytes.

8. The method according to claim 1, wherein the test lateral flow assay device comprises two or more lanes each comprising a separate sample receiving region and detection region.

9. The method according to claim 8, wherein the detection region of each lane detects the same analyte of the recombinant virus.

10. The method according to claim 8, wherein the detection region of each lane detects a different analyte of the recombinant virus.

11. The method according to claim 1, wherein the test lateral flow assay device comprises a reporter binding member positioned between the sample receiving region and the detection region, wherein the reporter binding member specifically binds to the recombinant virus.

12. The method according to claim 1, wherein the test lateral flow assay device comprises a control region downstream from the detection region.

13. The method according to claim 1, wherein the capture binding member is selected from the group consisting of: an antibody, a protein, a peptide, and a hapten.

14. The method according to claim 11, wherein the reporter binding member binds to the recombinant virus at a location that is different from the location to which the capture probe binds.

15. The method according to claim 11, wherein the reporter binding member comprises a label selected from the group consisting of a fluorescent dye, radio label, enzyme, and colorimetric label.

16. The method according to claim 1, wherein:
    the test lateral flow assay device comprises two or more lanes each comprising a separate sample receiving region and detection region; and
    the method further comprises applying a control sample to a sample receiving region of a control lateral flow assay device and reading a detection region of the control lateral flow assay device, wherein the control lateral flow assay device is identical to the test lateral flow assay device.

17. The method according to claim 1, wherein the recombinant virus is a retrovirus.

18. The method according to claim 17, wherein the retrovirus is a lentivirus.

19. The method according to claim 1, wherein the packaging cell line is transfected with one or more plasmid vectors of a viral vector packaging system.

20. The method according to claim 19, wherein the one or more plasmid vectors of the viral vector packaging system encode a viral envelope protein, a viral coat protein or both.

21. The method according to claim 19, wherein the transfecting comprises co-transfecting the packaging cell line with the plasmid and the one or more plasmid vectors of the viral vector packaging system.

* * * * *

UNITED STATES PATENT AND TRADEMARK OFFICE
CERTIFICATE OF CORRECTION

| | | |
|---|---|---|
| PATENT NO. | : 9,945,850 B2 | Page 1 of 1 |
| APPLICATION NO. | : 13/208267 | |
| DATED | : April 17, 2018 | |
| INVENTOR(S) | : Bisgrove et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 765 days.

Signed and Sealed this
Fifth Day of February, 2019

Andrei Iancu
*Director of the United States Patent and Trademark Office*